(12) United States Patent
Yakovlev

(10) Patent No.: US 9,511,025 B2
(45) Date of Patent: Dec. 6, 2016

(54) SYSTEM FOR THE DELIVERY OF BIOLOGICALLY ACTIVE COMPOUNDS INTO AN ORGANISM AND METHOD FOR THE PREPARATION OF SAID SYSTEM

(75) Inventor: Ruslan Jur'evich Yakovlev, Moscow (RU)

(73) Assignee: ZAKRYTOE AKTSIONERNOE OBSCHESTVO "ALMAZ PHARM", Moscow (RU)

( * ) Notice: Subject to any disclaimer, the term of this patent is extended or adjusted under 35 U.S.C. 154(b) by 160 days.

(21) Appl. No.: 14/235,052

(22) PCT Filed: Jul. 26, 2011

(86) PCT No.: PCT/RU2011/000552
§ 371 (c)(1),
(2), (4) Date: Jan. 25, 2014

(87) PCT Pub. No.: WO2013/015704
PCT Pub. Date: Jan. 31, 2013

(65) Prior Publication Data
US 2014/0328920 A1    Nov. 6, 2014

(51) Int. Cl.
| | |
|---|---|
| A61K 9/51 | (2006.01) |
| C01B 4/00 | (2006.01) |
| C01B 31/06 | (2006.01) |
| A61K 9/16 | (2006.01) |
| B82Y 5/00 | (2011.01) |
| A61K 47/02 | (2006.01) |
| A61K 47/48 | (2006.01) |
| A61K 33/00 | (2006.01) |
| A61K 31/132 | (2006.01) |
| A61K 31/197 | (2006.01) |
| C01B 31/02 | (2006.01) |

(52) U.S. Cl.
CPC .............. *A61K 9/16* (2013.01); *A61K 9/5115* (2013.01); *A61K 31/132* (2013.01); *A61K 31/197* (2013.01); *A61K 33/00* (2013.01); *A61K 47/02* (2013.01); *A61K 47/48023* (2013.01); *A61K 47/48884* (2013.01); *B82Y 5/00* (2013.01); *C01B 4/00* (2013.01); *C01B 31/0206* (2013.01); *C01B 31/06* (2013.01); *C01B 31/065* (2013.01); *Y10S 977/773* (2013.01)

(58) Field of Classification Search
CPC ........... A61K 49/0067; Y10S 977/773; Y10S 977/906
See application file for complete search history.

(56) References Cited

U.S. PATENT DOCUMENTS

| | | | |
|---|---|---|---|
| 4,160,746 A * | 7/1979 | Rashkin | 502/306 |
| 7,569,205 B1 * | 8/2009 | Hens et al. | 423/446 |
| 2003/0125283 A1 * | 7/2003 | Gatenby | 514/44 |
| 2004/0214159 A1 * | 10/2004 | Fujimura et al. | 435/5 |
| 2005/0158549 A1 * | 7/2005 | Khabashesku et al. | 428/403 |
| 2009/0226495 A1 | 9/2009 | Picardi et al. | |
| 2009/0283718 A1 * | 11/2009 | Yao | C01B 31/065 252/182.12 |
| 2010/0129457 A1 | 5/2010 | Razavi | |

OTHER PUBLICATIONS

GV Lisichkin, VV Korol'kov, BN Tarasevich, II Kulakova, AA Karpukhin. "Photochemical chlorination of nanodiamond and interaction of its modified surface with C-nucleophiles." Russian Chemical Bulletin, International Edition, vol. 55 No. 12, Dec. 2006, pp. 2212-2219.*
GV Lisichkin, II Kulakova, YA Gerasimov, AV Karpukhin, RY Yakovlev. "Halogenation of detonation-synthesised nanodiamond surfaces." Mendeleev Communications, vol. 19, 2009, pp. 309-310.*
GA Badun, MG Chernysheva, RY Yakovlev, NB Leonidov, MN Semenenko, GV Lisichkin. "A novel approach radiolabeling detonation nanodiamonds through the tritium thermal activation method." Radiochemica Acta, vol. 102(10), 2014, pp. 941-946.*
HA Girard, A El-Kharbachi, S Garcia-Argote, T Petit, P Bergonzo, B Rousseau, J-C Arnault. "Tritium labeling of detonation nanodiamonds." Chemical Communications, vol. 50, 2014, pp. 2916-2918.*
AR Dunn, DM Duffy, AM Stoneham. "A molecular dynamics study of diamond exposed to tritium bombardment for fusion applications." Nuclear Instruments and Methods in Physics Research B, vol. 269, 2011, pp. 1724-1726, available online Dec. 21, 2010.*
M.L. Hunnicutt and J.M. Harris, Reactivity of Organosilane Reagents on Microparitculate Silica, Analytical Chemistry, vol. 58, No. 4, Apr. 1986.
Takeo Ebina et al., , Comparative Study of XPS and DFT, J. Phys. Chem. B 1997, 101, 1125-1129.
Sheng, et al., Deposition of Copper Nanoparticles on Multiwalled Carbon Nanotubes, Front. Environ. Sci. Eng. DOI 10.1007/s11783-014-0711-8.

* cited by examiner

*Primary Examiner* — Isaac Shomer
(74) *Attorney, Agent, or Firm* — John Alumit

(57) ABSTRACT

The invention relates to the field of pharmaceutics, pharmaceutical nano-technology and pharmacology and concerns a system for delivering biologically active agents into an organism, the system comprising a nano-diamond with a particle size of 2-10 nm, the surface of said particles being modified by chlorine with a chlorine content of up to 14%, and to a method for producing said system.

2 Claims, 11 Drawing Sheets

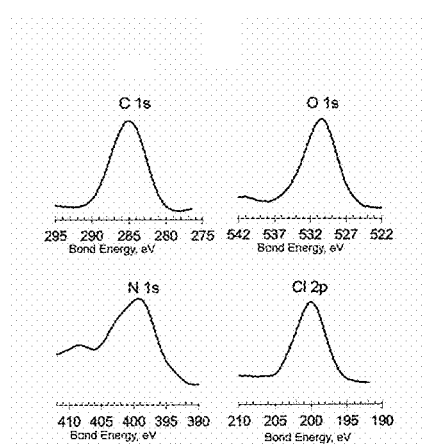

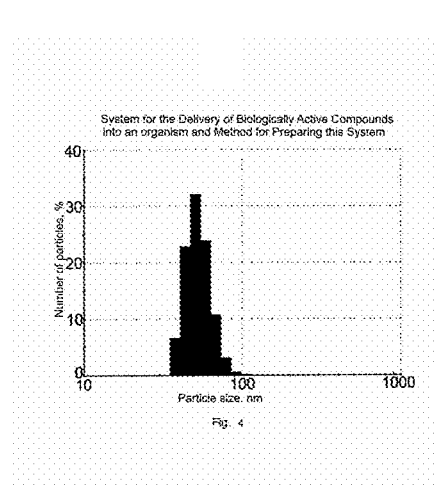

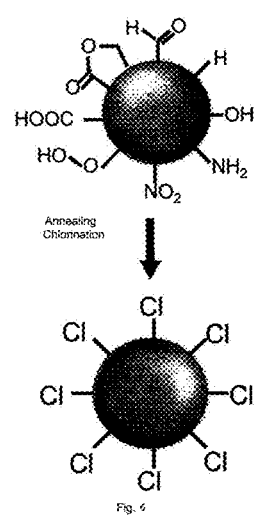

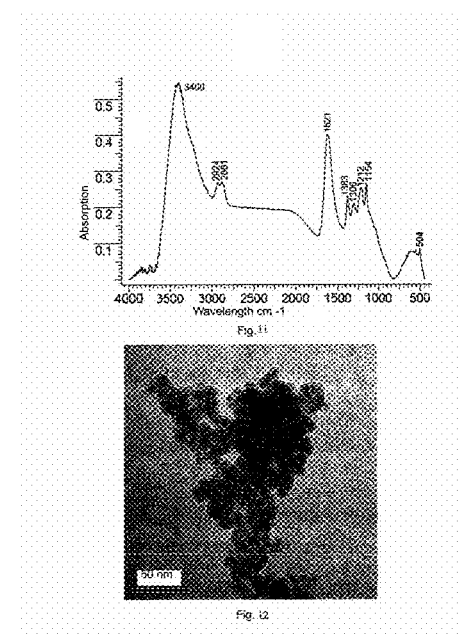
Fig. i1
Fig. i2

Fig. 13

SYSTEM FOR THE DELIVERY OF BIOLOGICALLY ACTIVE COMPOUNDS INTO AN ORGANISM AND METHOD FOR THE PREPARATION OF SAID SYSTEM

CROSS-REFERENCE TO RELATED APPLICATION

This application is a national stage application and claims the benefit of the priority filing date in PCT/RU2011/000552 referenced in WIPO Publication WO2013/015704 filed on Jul. 26, 2011. The earliest priority date claimed is Jul. 26, 2011.

FEDERALLY SPONSORED RESEARCH

Not Applicable

SEQUENCE LISTING OR PROGRAM

Not Applicable

BACKGROUND

The invention is directed to the fields of pharmaceutics, pharmaceutical nanotechnology and pharmacology and relates to a system for the delivery of biologically active compounds, including medicinal products, into an organism and to a method for the preparation of said system, wherein said invention can be used in medicine.

Systems for the delivery of biologically active compounds, including medicinal products, into an organism in the form of phospholipid nanoparticles with particle size of 10-30 nm, comprising phosphatidylcholine from plants and maltose (1), are known in the art.

Systems for the delivery of biologically active compounds, including medicinal products, into an organism as a combination thereof with a polymer excipient are known in the art. Nanoparticle-containing medications may be prepared by introducing a biologically active substance, or a medicinal product, during or after obtaining a polymeric dispersion. The active ingredients are dissolved, captured, or adsorbed on the surface of nanoparticles. A combination of said mechanisms is also possible [2]. However, polymer nanoparticles may have substantial disadvantages. With the exception of alkyl cyanoacrylate, most monomers form slowly biodegradable or non-biodegradable polymers. In addition, the molecular weight of the polymeric material cannot be fully controlled. The residues in the polymerization medium may be toxic, which would require a follow-up purification of the colloid system. Often, during polymerization, monomer molecules can react with medicinal product molecules, which results in the deactivation or destruction thereof [3].

A nanodiamond-based system for the delivery of medicinal products, with particle size of 5 nm, comprising an adsorbed antibiotic Doxorubicin and hydrated water molecules is known in the art [4].

A nanodiamond-based system for the delivery of medicinal products, comprising carboxylated nanodiamond particles with particle size of 3-5 nm, wherein $CH_2O(CH_2)6NH_2$-groups with the antitumor diterpenoid paclitaxel covalently bonded thereto attach to the surface of said nanodiamond in the course of several chemical transformations is known in the art [5].

Fluorine-modified nanodiamond particles with particle size of 2-10 nm containing up to 5% of fluorine at are known in the art [6]. The obtained nanodiamond that is modified with fluorine is used to prepare conjugants with such substances as alkyl lithium compounds, diamines, and amino acids. Said conjugants can be used as bonding agents in polymer compositions, abrasives and coatings, adsorbents, biosensors, and nanoelectromechanical systems.

A method for improving the efficacy of medicinal products by chemically (covalently) bonding the molecules of medicinal products to nanodiamond particles, 10 nm in size, via fluorine atoms and/or hydroxyl groups on the surface thereof is known in the art [7].

Fluorine atoms in an organic substance increase its toxicity; in particular, such substance can damage the nervous system, lungs, and liver. Despite being chemically inert, even the perfluorinated organic compounds alter the microsomal system of the xenobiotic biotransformation indicators (foreign bodies) in the liver [8]. Thus, the fluorine atoms covalently bound to the $C_{60}$ fullerene molecule, which is the closest nanostructured carbon analog of the nanodiamond, have been shown to increase its overall toxicity 2.4-5 times [9].

Thus, preparation of nanodiamond particles with no fluorine atom content, which could be used as a system for the delivery of biologically active substances into an organism, present an important and practically relevant task for medical and pharmaceutical industries.

A method to increase the efficacy of medicinal products by chemical (covalent) bonding of the medicinal product molecules with nanodiamond particles 10 nm in size via amino or acyl chloride groups on the surface thereof is known in the art [10].

Nanodiamond particles modified with chlorine, wherein the chlorine content is up to 12%, wherein the particle size in the suspension one month post synthesis is 70 nm, and 9 months post synthesis is 180 nm, respectively, are known in the art [11]. These particles are larger in size than the optimally sized particles required for medical use. In addition, this work was not able to produce the highest chlorine content on the nanodiamond's surface, which, in turn, would, subsequently, not yield a maximum content of the medicinal product on the nanodiamond's surface, which invariably reduces the efficacy of the delivery system. Although the inventors [11] point out that testing of nanodiamond samples, modified with chlorine, by the X-ray photoelectron spectroscopy (XPE) method confirm the bonding of chlorine atoms with the surface carbon atoms, the supporting data are not listed. In addition, the analysis of the IR-spectra presented in the article, which the inventors themselves conducted, does not confirm the presence of such chemical bonds. Purportedly, this is because the chlorine atoms are bound to the nanodiamond's surface by way of adsorption and not by covalent bonds. Consequently, medicinal products do not create sufficiently strong chemical bonds with said surface of the nanodiamond, and the system becomes inefficient.

The following method for the preparation of said nanodiamond's particles, modified with chlorine, and the embodiment thereof are also known in the art [11]. Chlorination of the nanodiamond's particles is conducted by liquid-phase chlorination of the reduced nanodiamond in a $CCl_4$ solution saturated with chlorine at room temperature with constant stirring for 72 hours and exposure to visible light. Upon chlorination, the nanodiamond particles are washed with dry $CCl_4$, centrifuged, and the residue is dried for 5-6 hours under 13-26 Pa pressure at 70-80° C.

In the embodiment of said method, the particles of nanodiamond modified with chlorine are prepared in the $CCl_4$ plasma for 4 hrs. [11].

The inventors [11] concluded that the bond they created between the chlorine atoms and the nanodiamond is less stable in air (due to the purported adsorption nature of the bond) than the bond between the nanodiamond and the fluorine atoms. In addition, the highest possible number of fluorine atoms bound to the surface of the nanodiamond is higher than that of chlorine atoms, which makes the chlorinated nanodiamond particles less favorable for the participation in the future covalent bonding reactions of chemical compounds as compared to the fluorinated nanodiamond particles.

Thus, the task of creating nanodiamond particles that do not contain fluorine and can effectively form covalent bonds with various biologically active compounds, comprising medicinal products, has been only partially solved. Moreover, a complete substitution of the chlorine atoms (covalently bound to the nanodiamond's surface with molecules of biologically active compounds) creates perspective systems for the delivery of biologically active compounds containing no halogen atoms on their surface, which inhibits uncontrollably increased toxic effects. This requirement is of utmost importance for any medicinal and medical products used in the medical and pharmaceutical industry.

SUMMARY

A system for the delivery of biologically active compounds into an organism according to the present invention is described as a grey ultradispersed nanodiamond powder (FIG. 1) with particle sizes of 2-10 nm (FIG. 2), wherein the surface of said particles is modified with chlorine, wherein the chlorine content is up to 14% (FIG. 3). In the claimed delivery system, distribution of the aggregate sizes in an aqueous suspension is 40-70 nm (FIG. 4.).

DRAWINGS

FIG. 1. Photomicrographs of the ultradispersed structure of the system for the delivery of biologically active compounds obtained by scanning with an electron microscope; a—23.83 thousand times magnification, b—8.57 thousand times magnification.

FIG. 2. Photomicrographs of the system for the delivery of biologically active compounds obtained by transmission electron microscopy.

FIG. 3. C 1s, O 1s, N 1s, Cl 2p XPE-spectra of the particle surfaces of the system for the delivery of biologically active compounds.

FIG. 4. Size distribution of the particles of the system for the delivery of biologically active compounds in an aqueous suspension prepared by the laser dynamic light scattering method.

FIG. 5. IR-spectrum of the system for the delivery of biologically active compounds.

FIG. 6. Preparation scheme for the system for the delivery of biologically active compounds.

FIG. 7. Preparation scheme for the nanodiamond and ethylenediamine conjugate.

FIG. 8. Preparation scheme for the nanodiamond and glycine conjugate.

FIG. 9. Raman-scattering spectrum of the nanodiamond and ethylenediamine conjugate.

FIG. 10. Biodistribution of the nanodiamond and ethylenediamine conjugate in rats.

FIG. 11. IR-spectrum of the nanodiamond and glycine conjugate.

FIG. 12. Photomicrograph of the nanodiamond and glycine conjugate obtained by the X-ray photoelectron spectroscopy method.

FIG. 13. Photomicrograph of the nanodiamond and glycine conjugate's penetration into the lymphoblast MOLT-4 cell; a and b—are the areas of particle penetration into cells.

DESCRIPTION

FIG. 1 clearly shows that the claimed delivery system possesses an ultradispersed structure created by particles with a diameter smaller than the resolution ability of the used instrument (from 20 nm). Photomicrographs were obtained on a super high resolution auto emission scanning electron microscope Zeiss Ultra Plus (Carl Zeiss, Germany). The conditions of the film taking are cited on the photomicrograph.

FIG. 3 shows XPE-spectra of the claimed system for the delivery of biologically active compounds. Said spectra define the nature, energy condition, and number of surface atoms of nanodiamond particles.

The surface of the claimed system for the delivery of biologically active compounds is examined on a LAS-3000 instrument (Riber, France) equipped with a hemispherical analyzer OPX-150. The non-monochromatized X-ray radiation from an aluminum anode (A1a=1486.6 eV) (12 kV voltage on the tube and 20 mA emission current) is used for photoelectron excitation. Calibration of the photoelectron peaks is conducted along the C 1s carbon line with 285 eV binding energy ($E_b$). Vacuum in the work chamber is $6.7 \times 10^{-8}$ Pa. High vacuum is achieved with an ion pump.

The elemental composition on the surface of the claimed system for the delivery of biologically active compounds according to the XPE data is shown in Table 1.

TABLE 1

Elemental composition and surface atom-binding energy of the claimed system for the delivery of biologically active compounds.

| Name of the Characteristics | Chemical Elements | | | |
|---|---|---|---|---|
| | C | O | N | Cl |
| At % | 76.7-91.2 | 5.0-7.1 | 1.8-2.2 | 2-4 |
| Binding energy, eV | 285.3 ± 0.5 | 530.7 ± 0.5 | 399.5 ± 0.5<br>408.7 ± 0.5 | 200.3 ± 0.5 |

FIG. 4 shows the distribution curve of particle sizes in an aqueous suspension of the claimed system for the delivery of biologically active compounds, wherein the aggregate sizes are 40-70 nm.

Distribution of particle sizes in the aqueous suspension of the claimed delivery system is determined by laser dynamic light scattering on a ZetaSizer instrument (Malvem Instruments, USA).

Figure 5A:
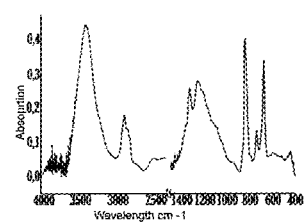
Figure 5B:
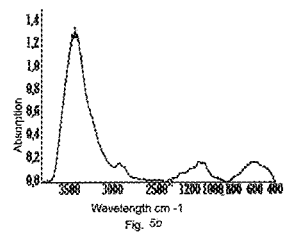

FIG. 5a shows an IR-spectrum of the claimed system for the delivery of biologically active compounds, wherein the content of chlorine on the surface is 14%. The spectrum shows a broad intense band with a maximum at 3,430 $cm^{-1}$; a broad band with a maximum at 1,262 $cm^{-1}$; five bands of medium intensity at 2,929, 2,892, 1,131, 846, and 680 $cm^{-1}$;

and a weak signal at 743 cm$^{-1}$. Said spectrum confirms the presence of covalently bound chlorine atoms on the surface of the claimed delivery system, the characteristic valence frequencies of said chlorine atoms are in the 650-850 cm$^{-1}$ range [12]. FIG. 5b shows an IR-spectrum of the claimed system for the delivery of biologically active compounds with a minimal chlorine content on the surface (0.1%). The spectrum shows a broad intense band with a maximum at 3,430 cm$^{-1}$; two broad bands with maximums at 1,136 and 621 cm$^{-1}$; two bands of medium intensity at 2,929 and 2,892 cm$^{-1}$; and a weak signal at 1,331 cm$^{-1}$. Such low chlorine concentration on the surface of the claimed system for the delivery of biologically active compounds does not show on the IR-spectrum in the 650-850 cm$^{-1}$ range.

IR-spectra were registered on a FTIRS IR200 Thermonicolet instrument (Thermo Scientific, USA). Resolution—2 cm$^{-1}$, number of scans—64. For testing, carefully weighed samples were mixed with the KBr powder and pressed into a tablet.

Because the obtained system is not hazardous to humans and does not contain animals fluorine and fluorine compounds, which are left after biologically active compounds are bound to the nanodiamond's surface, the system can be effectively used for the delivery of biologically active compounds, including medicinal products, to humans.

Figure 6:
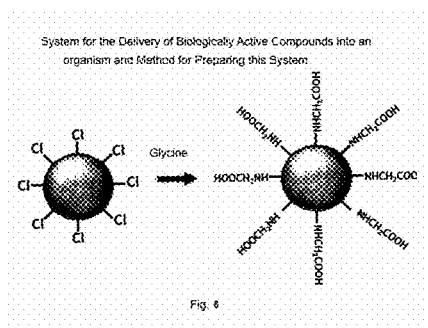

The invention also claims a method for preparing the system for delivery of biologically active compounds; the scheme thereof is shown on FIG. 6.

The claimed method for preparing the system for delivery of biologically active compounds into an organism comprises annealing of nanodiamond particles at 500-1,200° C. in a hydrogen gas stream and subsequent chlorination of the obtained annealed particles of the nanodiamond with molecular chlorine dissolved in CCl$_4$ under visible light at temperatures ranging from 50 to 70° C. Annealing is conducted at a speed of the hydrogen gas of 2-3 L/hour. Chlorination is conducted largely between 36 to 60 hours with a molecular chlorine concentration in CCl$_4$ of 3 to 5 wt %, followed by centrifugation, washing with CCl$_4$, and drying.

More precisely, the method comprises annealing of the nanodiamond in a hydrogen gas stream at 2-3 L/hour at 500-1,200° C. for 1-8 hours. The annealed particles of the nanodiamond are then chlorinated in a liquid phase with molecular chlorine. For that, chlorine obtained in the reaction between K$_2$Cr$_2$O$_7$ (or KMnO$_4$) and hydrochloric acid is dissolved in CCl$_4$ to 3-5 wt %. Chlorination is conducted by photochemical exposure to visible light for 36-60 hours at 50-70° C. The suspension is then centrifuged at over 6,000 rpm, washed with CCl$_4$, the process is repeated 3-5 times, and the residue is dried in a vacuum to constant weight.

The resulting delivery system is used to prepare conjugates with biologically active compounds, including medicinal products, from various pharmacological groups comprising: alkylating agents, in particular those containing ethylene diamines, excipients, reagents and intermediate products, and also amino acids.

Figure 7:
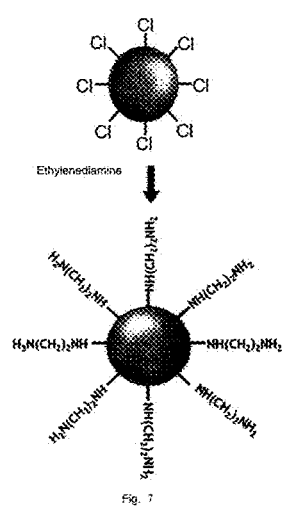

For diamines, the obtained particles of the claimed delivery system are suspended in dimethyl sulfoxide (CH$_3$)$_2$SO; ethylenediamine is then added to the resulting suspension, followed by the addition of several drops of pyridine, and said suspension is kept at 120° C. for 24 hours. [FIG. 7]. The resulting conjugate of the nanodiamond and ethylenediamine is then centrifuged at over 6,000 rpm, washed with water and acetone multiple times, and dried in a vacuum to constant weight.

Said conjugate is used to deliver ethylenediamine to an organism. To prove that the set objective has been met, in preparation of said system for the delivery of biologically active compounds into an organism, after annealing, the nanodiamond is labeled with tritium by the thermal activation method [13]. The system for the delivery of biologically active compounds with a radioactive label on its surface is then prepared according to the present invention. A conjugate of said delivery system with ethylenediamine is then prepared following the aforementioned method. Said conjugate with the radioactive label is then intraperitoneally administered to a rat. The rat is euthanized, its organs are extracted, homogenized, and the radioactivity of the obtained homogenate is measured on a liquid scintillation spectrometer.

For amino acids, with glycine as an example, the conjugate thereof with the delivery system is prepared according to the following procedure (FIG. 8): The obtained particles of the delivery system are dissolved in a polar water-organic solvent or in water. Glycine, as amino acetic acid NH$_2$CH$_2$COOH, and tertiary amine are then added to the obtained suspension. Organic solvents that dissolve glycine, such as pyridine or lower aliphatic alcohols, are preferred. The obtained mixture is treated with ultrasound (50 W) for 5-60 minutes, and then kept at 50-80° C. with constant stirring for 12-48 hours. The resulting product is centrifuged at 6,000 rpm, washed with ethanol, and the residue is dried in a vacuum overnight at 70° C.

The obtained conjugate is used to deliver glycine to an organism. For that, the reaction between the obtained conjugate and cellular cultures is studied under the electron microscope by cellular biology methods.

The invention is illustrated by the following examples.

Example 1

A 200 mg sample of nanodiamond is annealed in a hydrogen gas stream at 2.5 L/hr. and 800° C. for 5 hours. The annealed nanodiamond particles are subjected to liquid-phase chlorination with molecular chlorine (4.7 wt %) in 40 ml of CCl$_4$ under exposure to visible light for 48 hours at 60° C. The suspension is then centrifuged at 8,000 rpm and washed with dry CCl$_4$. The process is repeated 4 times, and the resulting residue is dried in a vacuum to constant weight. The yield of the final product is 181 mg (90.5%).

The obtained product is a grey ultradispersed powder with particle sizes of 2-10 nm, containing up to 14% chlorine on its surface, wherein the size of the aggregates thereof in an aqueous suspension is 50 nm, said product is characterized by IR-spectroscopy: a broad intense band with a maximum at 3,430 cm$^{-1}$, a broad band with a maximum at 1,262 cm$^{-1}$, five moderately intense bands at 2,929, 2,892, 1,331, 846, 680 cm$^{-1}$, and a weak signal at 743 cm$^{-1}$. The elemental composition of the surface is as follows: C-78.1, O-6.0, N-1.9, Cl-14%, respectively.

Example 2

A 250 mg sample of nanodiamond is annealed in a hydrogen gas stream at 2.4 L/hr. and 800° C. for 5 hours. The annealed nanodiamond particles are subjected to liquid-phase chlorination with molecular chlorine (4.8 wt %) in 50 ml of CCl$_4$ under exposure to visible light for 36 hours at 60° C. The suspension is then centrifuged at 8,000 rpm and washed with dry CCl$_4$. The process is repeated 3 times, and the resulting residue is dried in a vacuum to constant weight. The yield of the final product is 198 mg (79.1%).

The obtained product is a grey ultradispersed powder with particle sizes of 2-10 nm, containing 4.2% chlorine on its surface, wherein the size of the aggregates thereof in an aqueous suspension is 67 nm, said product is characterized by IR-spectroscopy: a broad intense band with a maximum at 3,430 $cm^{-1}$, a broad band with a maximum at 1,262 $cm^{-1}$, five moderately intense bands at 2,929, 2,892, 1,331, 846, 680 $cm^{-1}$, and a weak signal at 743 $cm^{-1}$. The elemental composition of the surface is as follows: C-87.9, O-5.9, N-2.0, Cl-4.2%, respectively.

Example 3

A 400 mg sample of nanodiamond is annealed in a hydrogen gas stream at 2.7 L/hour and 800° C. for 5 hours. The annealed nanodiamond particles are subjected to liquid-phase chlorination with molecular chlorine (3.5 wt %) in 80 ml of $CCl_4$ under exposure to visible light for 60 hours at 60° C. The suspension is then centrifuged at 7,000 rpm and washed with dry $CCl_4$. The process is repeated 3 times, and the resulting residue is dried in a vacuum to constant weight. The yield of the final product is 339.6 mg (84.9%).

The obtained product is a grey ultradispersed powder with particle sizes of 2-10 nm, containing 7.8% chlorine on its surface, wherein the size of the aggregates thereof in an aqueous suspension is 56 nm, said product is characterized by IR-spectroscopy: a broad intense band with a maximum at 3,430 $cm^{-1}$, a broad band with a maximum at 1,262 $cm^{-1}$, five moderately intense bands at 2,929, 2,892, 1,331, 846, 680 $cm^{-1}$, and a weak signal at 743 $cm^{-1}$. The elemental composition of the surface is as follows: C-84.1, O-6.3, N-1.8, Cl-7.8%, respectively.

Example 4

A 200 mg sample of nanodiamond is annealed in a hydrogen gas stream at 2.0 L/hr. and 800° C. for 5 hours. The annealed nanodiamond particles are subjected to liquid-phase chlorination with molecular chlorine (5.0 wt %) in 40 ml of $CCl_4$ under exposure to visible light for 48 hrs. at 50° C. The suspension is then centrifuged at 6,000 rpm and washed with dry $CCl_4$. The process is repeated 5 times, and the resulting residue is dried in a vacuum to constant weight. The yield of the final product is 149.2 mg (74.6%).

The obtained product is a grey ultradispersed powder with particle sizes of 2-10 nm, containing 3.0% chlorine on its surface, wherein the size of the aggregates thereof in an aqueous suspension is 70 nm, said product is characterized by IR-spectroscopy: a broad intense band with a maximum at 3,430 $cm^{-1}$, a broad band with a maximum at 1,262 $cm^{-1}$, five moderately intense bands at 2,929, 2,892, 1,331, 846, 680 $cm^{-1}$, and a weak signal at 743 $cm^{-1}$. The elemental composition of the surface is as follows: C-87.8, O-7.1, N-2.1, Cl-3.0%, respectively.

Example 5

A 200 mg sample of nanodiamond is annealed in a hydrogen gas stream at 2.9 L/hour and 800° C. for 5 hours. The annealed nanodiamond particles are subjected to liquid-phase chlorination with molecular chlorine (5.0 wt %) in 40 ml of $CCl_4$ under exposure to visible light for 48 hrs. at 70° C. The suspension is then centrifuged at 9,000 rpm and washed with dry $CCl_4$. The process is repeated 3 times, and the resulting residue is dried in a vacuum to constant weight. The yield of the final product is 144.6 mg (72.3%).

The obtained product is a grey ultradispersed powder with particle sizes of 2-10 nm, containing 9.4% chlorine on its surface, wherein the size of the aggregates thereof in an aqueous suspension is 61 nm, said product is characterized by IR-spectroscopy: a broad intense band with a maximum at 3,430 $cm^{-1}$, a broad band with a maximum at 1,262 $cm^{-1}$, five moderately intense bands at 2,929, 2,892, 1,331, 846, 680 $cm^{-1}$, and a weak signal at 743 $cm^{-1}$. The elemental composition of the surface is as follows: C-83.3, O-5.5, N-1.8, Cl-9.4%, respectively.

Example 6

A 500 mg sample of nanodiamond is annealed in a hydrogen gas stream at 2.5 L/hour and 500° C. for 5 hours. The annealed nanodiamond particles are subjected to liquid-phase chlorination with molecular chlorine (5.0 wt %) in 100 ml of $CCl_4$ under exposure to visible light for 48 hours at 60° C. The suspension is then centrifuged at 6,000 rpm and washed with dry $CCl_4$. The process is repeated 5 times, and the resulting residue is dried in a vacuum to constant weight. The yield of the final product is 433.5 mg (86.7%).

The obtained product is a grey ultradispersed powder with particle sizes of 2-10 nm, containing 5.2% chlorine on its surface, wherein the size of the aggregates thereof in an aqueous suspension is 63 nm, said product is characterized by IR-spectroscopy: a broad intense band with a maximum at 3,430 $cm^{-1}$, a broad band with a maximum at 1,262 $cm^{-1}$, five moderately intense bands at 2,929, 2,892, 1,331, 846, 680 $cm^{-1}$, and a weak signal at 743 $cm^{-1}$. The elemental composition of the surface is as follows: C-86.5, O-6.1, N-2.2, Cl-5.2%, respectively.

Example 7

A 500 mg sample of nanodiamond is annealed in a hydrogen gas stream at 2.5 L/hour and 1,200° C. for 5 hours. The annealed nanodiamond particles are subjected to liquid-phase chlorination with molecular chlorine (3.3 wt %) in 100 ml of $CCl_4$ under exposure to visible light for 48 hours at 60° C. The suspension is then centrifuged at 7,000 rpm and washed with dry $CCl_4$. The process is repeated 4 times, and the resulting residue is dried in a vacuum to constant weight. The yield of the final product is 370.5 mg (74.1%).

The obtained product is a grey ultradispersed powder with particle sizes of 2-10 nm, containing 8.8% chlorine on its surface, wherein the size of the aggregates thereof in an aqueous suspension is 58 nm, said product is characterized by IR-spectroscopy: a broad intense band with a maximum at 3,430 $cm^{-1}$, a broad band with a maximum at 1,262 $cm^{-1}$, five moderately intense bands at 2,929, 2,892, 1,331, 846, 680 $cm^{-1}$, and a weak signal at 743 $cm^{-1}$. The elemental composition of the surface is as follows: C-83.9, O-5.5, N-1.8, Cl-8.8%, respectively.

Example 8

A 200 mg sample of nanodiamond is annealed in a hydrogen gas stream at 2.0 L/hour and 800° C. for 1 hour. The annealed nanodiamond particles are subjected to liquid-phase chlorination with molecular chlorine (4.6 wt %) in 40 ml of $CCl_4$ under exposure to visible light for 48 hours at 60° C. The suspension is then centrifuged at 9,000 rpm and washed with dry $CCl_4$. The process is repeated 3 times, and the resulting residue is dried in a vacuum to constant weight. The yield of the final product is 180 mg (90.0%).

The obtained product is a grey ultradispersed powder with particle sizes of 2-10 nm, containing 3.5% chlorine on its surface, wherein the size of the aggregates thereof in an aqueous suspension is 70 nm, said product is characterized by IR-spectroscopy: a broad intense band with a maximum at 3,430 cm$^{-1}$, a broad band with a maximum at 1,262 cm$^{-1}$, five moderately intense bands at 2,929, 2,892, 1,331, 846, 680 cm$^{-1}$, and a weak signal at 743 cm$^{-1}$. The elemental composition of the surface is as follows: C-87.5, O-6.9, N-2.1, Cl-3.5%, respectively.

Example 9

A 300 mg sample of nanodiamond is annealed in a hydrogen gas stream at 2.0 L/hour and 800° C. for 8 hours. The annealed nanodiamond particles are subjected to liquid-phase chlorination with molecular chlorine (4.6 wt %) in 60 ml of CCl$_4$ under exposure to visible light for 48 hours at 60° C. The suspension is then centrifuged at 6,000 rpm and washed with dry CCl$_4$. The process is repeated 5 times, and the resulting residue is dried in a vacuum to constant weight. The yield of the final product is 256.2 mg (85.4%).

The obtained product is a grey ultradispersed powder with particle sizes of 2-10 nm, containing 13.2% chlorine on its surface, wherein the size of the aggregates thereof in an aqueous suspension is 55 nm, said product is characterized by IR-spectroscopy: a broad intense band with a maximum at 3,430 cm$^{-1}$, a broad band with a maximum at 1,262 cm$^{-1}$, five moderately intense bands at 2,929, 2,892, 1,331, 846, 680 cm$^{-1}$, and a weak signal at 743 cm$^{-1}$. The elemental composition of the surface is as follows: C-79.8, O-5.2, N-1.8, Cl-13.2%, respectively.

Characteristics of the system for the delivery of biologically active compounds and parameters of the procedure by which it is prepared are listed in Table 2 for each of the examples.

Example 10

A 500 mg sample of the claimed delivery system prepared according to the procedure described in Example 1 is suspended in 50 ml of the solvent dimethyl sulfoxide; 2.5 ml of ethylenediamine are added to the resulting suspension followed by the addition of 2 drops of pyridine, and the suspension is then kept at 120° C. for 24 hours. The resulting conjugate of the nanodiamond and ethylenediamine is then centrifuged at 6,000 rpm, washed with water and acetone 5 times, and dried in a vacuum to constant weight.

Figure 9:
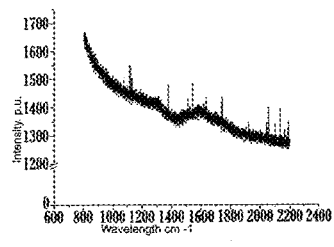

The obtained conjugate is a grey ultradispersed powder with particle sizes of 2-10 nm, characterized by Raman Scattering with strong luminescence exceeding the intensity of the nanodiamond's R-spectrum more than 50 times (FIG. 9). The elemental composition of the surface is as follows: C-86.4, C-8.9, N-4.7%, respectively.

The obtained conjugate is used to deliver ethylenediamine into an organism.

To achieve said objective when preparing the system for the delivery of biologically active compounds, the annealed nanodiamond is labeled with tritium by the thermal activation method [13]. After the annealed nanodiamond has been labeled with tritium, it is kept in water for 48 hours, centrifuged, and the supernatant is separated and combined with a new portion of the solvent. The resulting product is a preparation of the annealed nanodiamond with the specific radioactivity of 90 Gbq/g. The system for the delivery of biologically active compounds with a radioactive label on its surface is then prepared according to the claimed method. A conjugate of the delivery system with ethylenediamine is subsequently prepared according to the method described above. The prepared radioactively labeled conjugate is then intraperitoneally administered to a rat (white outbred male, 400 g weight) as an aqueous suspension. Four hours later, the animal is euthanized, its internal organs and tissues are

TABLE 2

Table summarizing characteristics of the claimed system for the delivery of biologically active compounds and conditions of its preparation.

Figure 10:
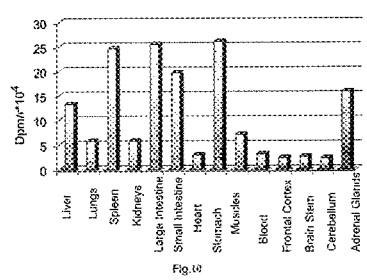

| Process Parameters | Example #/Process Conditions | | | | | | | | |
|---|---|---|---|---|---|---|---|---|---|
| | 1 | 2 | 3 | 4 | 5 | 6 | 7 | 8 | 9 |
| Annealing Time (1-8), hr. | 5 | 5 | 5 | 5 | 5 | 5 | 5 | 1 | 8 |
| Annealing Temperature (500-1200), ° C. | 800 | 800 | 800 | 800 | 800 | 500 | 1200 | 800 | 800 |
| Chlorination Time (36-60), hr. | 48 | 36 | 60 | 48 | 48 | 48 | 48 | 48 | 48 |
| Chlorination Temperature (50-70), hr. | 60 | 60 | 60 | 50 | 70 | 60 | 60 | 60 | 60 |
| Product Yield, % | 90.5 | 79.1 | 84.9 | 74.6 | 72.3 | 86.7 | 74.1 | 90.0 | 85.4 |
| Delivery System Characteristics | | | | | | | | | |
| Chlorine Content, at % | 14 | 4.2 | 7.8 | 3.0 | 9.4 | 5.2 | 8.8 | 3.5 | 13.2 |
| Particle Size in Suspension, nm | 50 | 67 | 56 | 70 | 61 | 63 | 58 | 70 | 55 | extracted and weighed, homogenized in aqueous NaOH and $H_2O_2$ solutions, and the radioactivity of the obtained homogenate is measured on a RackBeta 1215 (Finland) liquid scintillation spectrometer (Table 3, FIG. 10).

TABLE 3

List of the organs extracted from the rat to study distribution of the nanodiamond and ethylenediamine conjugate

| Sample # | Type of Organ or Tissue | Weight, g | NaOH amount, ml | $H_2O_2$ amount, ml |
|---|---|---|---|---|
| 1 | Liver | 0.42 | 2 | 0.05 |
| 2 | Lungs | 0.13 | 1.5 | — |
| 3 | Spleen | 0.26 | 2 | 0.15 |
| 4 | Kidneys | 0.22 | 1.5 | 0.05 |
| 5 | Large Intestine | 0.17 | 2 | — |
| 6 | Small Intestine | 0.12 | 1 | — |
| 7 | Heart | 0.27 | 2.05 | 0.05 |
| 8 | Stomach | 0.08 | 1.5 | — |
| 9 | Muscles | 0.1 | 1.5 | — |
| 10 | Blood | 0.27 | 3 | 0.25 |
| 12 | Frontal Cortex | 0.18 | 1.5 | — |
| 13 | Brain Stem | 0.31 | 2 | 0.05 |
| 15 | Cerebellum | 0.32 | 2.5 | 0.05 |
| 16 | Adrenal Glands | 0.08 | 1 | — |

It is evident from FIG. 10 that the nanodiamond and ethylenediamine conjugate is distributed practically throughout all vital organs, while passing through the hematoencephalic barrier in different quantitative ratios.

Example 11

200 mg of the claimed delivery system prepared according to the method described in Example 1 are suspended in 40 ml of water-alcohol mixture (water:methanol=1:1), 300 mg of glycerin as free amino acid $NH_2CH_2COOH$ and 1 ml triethylamine are then added to the resulting suspension. The resulting mixture is treated with ultrasound (50 W) for 40 minutes and kept at 65° C. with constant stirring for 30 hours. The resulting product is centrifuged at 6,000 rpm, washed with ethanol, and dried in a vacuum at 70° C. overnight. The residual moisture content of the product is 2.2%. The yield of the final product is 186 mg (93%).

Figure 1:
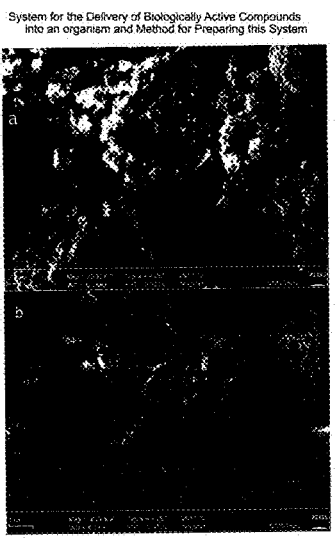
Figure 2:
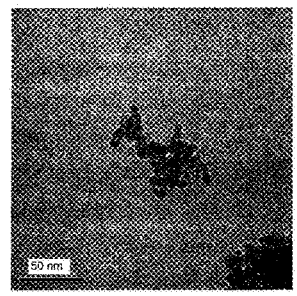
FIG. 2 shows that the claimed system for the delivery of biologically active compounds has the particle size distribution of 2-10 nm. Photomicrographs were obtained on a transmission electron microscope Jeol 1011 (JEOL, Japan).

The obtained product is an ultradispersed powder, dark grey with a bluish tint, with 2-10 nm primary particle sizes and a surface layer membrane measuring up to 1 nm (FIG. 1), said product is characterized by IR-spectroscopy: a broad intense band with a maximum at 3,400 $cm^{-1}$, a strong signal at 1,621 $cm^{-1}$, six moderately intense bands at 2,924, 2,881, 1,383, 1,306, 1,212, and 1,154 $cm^{-1}$, and a weak signal at 504 $cm^{-1}$ (FIG. 12). The elemental composition of the surface is as follows: C-91.5, O-6.0, N-2.5%, respectively.

Figure 13:
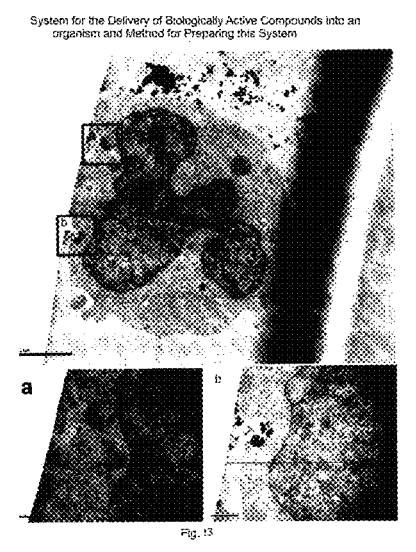

The obtained conjugate is used for the delivery of glycine into an organism. The presence of the nanodiamond and glycine conjugate in an organism is confirmed by electron microscopy in the reaction thereof with the lymphoblast MOLT-4 cell culture. FIG. 13 demonstrates that the conjugate causes invagination of the lymphoblast's cellular membrane and subsequent penetration thereof into the cytosol.

REFERENCES

1. RFPat RU 2391966, C1 Jun. 20, 2010
2. Nanotherapeutics. Drug delivery concepts in nanoscience. Translated from the English. Edited by Alf Lamprecht, M.: Nauchny Mir, 2010, pp. 10-20.
3. J. L. Grangier, M. Puygrenier, J. C. Gautier, P. Couvreur. Nanoparticles as carriers for growth hormone releasing factors//J. Control. Rel. 1991. V.15, pp. 3-13.
4. A. Adnant, R. Lam, H. Chen et al. Atomistic Simulation and Measurement of pH Dependent Cancer Therapeutic Interactions with Nanodiamond Carrier//Mol. Pharmaceutics. 2001. V. 8., pp. 368-374.
5. K.-K. Liy, W.-W. Zheng, C.-C. Wang et al. Covalent linkage of nanodiamond-paclitaxel for drug delivery and cancer therapy//Nanotechnology. 2010. V. 21. #315106. 14 pp.
6. USPat 2005/0158549 A1, Jul. 21, 2005.
7. USPat 2010/0129457 A1, May 27, 2010.
8. Russian encyclopedia of job safety. 3 volumes. $2^{nd}$ edition. Revised and enlarged edition, Volume 3. M: pub. NTs ENAS. 2007, p. 181.
9. N. N. Karkischenko, Nanoengineered drugs: Novel biomedical initiatives in pharmacology//Biomeditsina, 2009, N2, pp. 5-26.
10. USPat 2009/0226495 A1, Sep. 10, 2009.
11. G. V. Lisichkin, I. I. Kulakova, Y. A. Gerasimov et al. Halogenation of detonation-synthesized nanodiamond surfaces. Mendeleev Commun. 2009. V. 19, pp. 309-310.
12. A. Smith. Applied IR-spectroscopy. Translated from the English. M.: Mir, 1982, p. 307.
13. G. A. Badun. Compounds labeled with tritium./Methodological guidelines. M., MSU, 2008, pp. 36-37.

What is claimed:

1. A system for delivery of biologically active compounds into an organism, comprising nanodiamond with particles sizes between 2-10 nm, wherein a surface of said particles is modified with tritium, wherein a radioactivity of tritium constitutes no less than 90 GBq/g.

2. A method for preparing a system for delivery of biologically active compounds into an organism, comprising nanodiamond with particles sizes between 2-10 nm, wherein a surface of said particles is modified with tritium, wherein a radioactivity of tritium constitutes no less than 90 GBq/g, said method comprising the step of annealing the nanodiamond particles in a stream of hydrogen gas and modification of obtained particles with tritium using the thermal activation method of tritium.

* * * * *